(12) United States Patent
Tan et al.

(10) Patent No.: US 11,767,343 B2
(45) Date of Patent: Sep. 26, 2023

(54) PEPTIDE PROBE FOR RECOGNITION OF G-QUADRUPLEX AND USE THEREOF IN DETECTION OF G-QUADRUPLEX IN CELL

(71) Applicant: Changzhi Medical College, Changzhi (CN)

(72) Inventors: Zheng Tan, Changzhi (CN); Kewei Zheng, Changzhi (CN); Jinping Zheng, Changzhi (CN)

(73) Assignee: CHANGZHI MEDICAL COLLEGE, Changzhi (CN)

( * ) Notice: Subject to any disclaimer, the term of this patent is extended or adjusted under 35 U.S.C. 154(b) by 426 days.

(21) Appl. No.: 16/896,196

(22) Filed: Jun. 8, 2020

(65) Prior Publication Data
US 2021/0403507 A1   Dec. 30, 2021

(30) Foreign Application Priority Data
May 15, 2020 (CN) .......................... 202010413944.7

(51) Int. Cl.
| | |
|---|---|
| *C07K 14/00* | (2006.01) |
| *C07K 14/47* | (2006.01) |
| *C07K 19/00* | (2006.01) |
| *C12Q 1/68* | (2018.01) |
| *C07K 7/06* | (2006.01) |
| *C12Q 1/6869* | (2018.01) |

(52) U.S. Cl.
CPC ................ *C07K 7/06* (2013.01); *C07K 14/00* (2013.01); *C07K 14/47* (2013.01); *C12Q 1/68* (2013.01); *C12Q 1/6869* (2013.01); *C07K 2319/80* (2013.01); *C07K 2319/85* (2013.01); *C12Q 2565/133* (2013.01)

(58) Field of Classification Search
CPC . C07K 4/00; C07K 7/08; C07K 14/00; C07K 14/47; C07K 2319/80; C07K 2319/85; C12N 9/14; C12Q 1/68; C12Q 1/6809; C12Q 1/6869; C12Q 2522/10; C12Q 2565/133
See application file for complete search history.

(56) References Cited

U.S. PATENT DOCUMENTS

2016/0115201 A1* 4/2016 Phan ...................... C07K 14/00
435/6.12

OTHER PUBLICATIONS

Sun et al. Developing Novel G-Quadruplex Ligands: From Interaction with Nucleic Acids to Interfering with Nucleic Acid-Protein Interaction. Molecules. 2019, vol. 24, 396, 29 pages. (Year: 2019).*

* cited by examiner

*Primary Examiner* — Jeffrey E. Russel
(74) *Attorney, Agent, or Firm* — MATTHIAS SCHOLL P.C.; Matthias Scholl

(57) ABSTRACT

A polypeptide probe for detecting G-quadruplexes (G4s), includes: from two to four G4-binding domains, and one or more linkers disposed between every two G4-binding domains. Each G4-binding domain includes a specific motif including a sequence of amino acids PGHLKGREIGMWY (SEQ ID NO: 1).

11 Claims, 10 Drawing Sheets

Specification includes a Sequence Listing.

SEQUENCE LISTING

<160> NUMBER OF SEQ ID NOS: 74

<210> SEQ ID NO 1
<211> LENGTH: 13
<212> TYPE: PRT
<213> ORGANISM: Artificial Sequence
<220> FEATURE:
<223> OTHER INFORMATION: Fully synthetic

<400> SEQUENCE: 1

Pro Gly His Leu Lys Gly Arg Glu Ile Gly Met Trp Tyr
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Fully synthetic

<400> SEQUENCE: 2

His Pro Gly His Leu Lys Gly Arg Glu Ile Gly Met Trp Tyr Ala Lys
1               5                   10                  15

Lys Gln Gly Gln Lys Asn Lys
            20

<210> SEQ ID NO 3
<211> LENGTH: 348
<212> TYPE: DNA
<213> ORGANISM: Artificial Sequence
<220> FEATURE:
<223> OTHER INFORMATION: Fully synthetic

<400> SEQUENCE: 3
atgggcagca gccatcatca tcatcatcac agcagcggcc tggtgccgcg cggcagccat      60
atgcatcctg gccatctcaa aggccgtgaa atcggcatgt ggtacgctaa gaaacagggt     120
cagaaaaaca aaggcacggg aagcggcgca ggcaccggca gcggtgcggg taccggctcc     180
ggcgcacatc caggccacct gaaaggacgc gagatcggta tgtggtacgc aaagaaacag     240
ggtcagaaga taaaggcac cggttccggt gcagactaca agaccatga cggtgattat      300 aaagatcatg acatcgatta caaggatgac gatgacaagt aagaattc                 348

<210> SEQ ID NO 4
<211> LENGTH: 113
<212> TYPE: PRT
<213> ORGANISM: Artificial Sequence
<220> FEATURE:
<223> OTHER INFORMATION: Fully synthetic

<400> SEQUENCE: 4

Met Gly Ser Ser His His His His His His Ser Ser Gly Leu Val Pro
1               5                   10                  15

Arg Gly Ser His Met His Pro Gly His Leu Lys Gly Arg Glu Ile Gly
                20                  25                  30

Met Trp Tyr Ala Lys Lys Gln Gly Gln Lys Asn Lys Gly Thr Gly Ser
            35                  40                  45

Gly Ala Gly Thr Gly Ser Gly Ala Gly Thr Gly Ser Gly Ala His Pro
        50                  55                  60

Gly His Leu Lys Gly Arg Glu Ile Gly Met Trp Tyr Ala Lys Lys Gln
65                  70                  75                  80

Gly Gln Lys Asn Lys Gly Thr Gly Ser Gly Ala Asp Tyr Lys Asp His
                85                  90                  95

Asp Gly Asp Tyr Lys Asp His Asp Ile Asp Tyr Lys Asp Asp Asp Asp
            100                 105                 110

Lys

<210> SEQ ID NO 5
<211> LENGTH: 72
<212> TYPE: PRT
<213> ORGANISM: Artificial Sequence
<220> FEATURE:
<223> OTHER INFORMATION: Fully synthetic

```
<400> SEQUENCE: 5

Met Gly Ser Ser His His His His His Ser Ser Gly Leu Val Pro
1               5                   10                  15

Arg Gly Ser His Met His Pro Gly His Leu Lys Gly Arg Glu Ile Gly
                20                  25                  30

Met Trp Tyr Ala Lys Lys Gln Gly Gln Lys Asn Lys Gly Thr Gly Ser
            35                  40                  45

Gly Ala Asp Tyr Lys Asp His Asp Gly Asp Tyr Lys Asp His Asp Ile
    50                  55                  60

Asp Tyr Lys Asp Asp Asp Asp Lys
65                  70

<210> SEQ ID NO 6
<211> LENGTH: 154
<212> TYPE: PRT
<213> ORGANISM: Artificial Sequence
<220> FEATURE:
<223> OTHER INFORMATION: Fully synthetic

<400> SEQUENCE: 6

Met Gly Ser Ser His His His His His Ser Ser Gly Leu Val Pro
1               5                   10                  15

Arg Gly Ser His Met His Pro Gly His Leu Lys Gly Arg Glu Ile Gly
                20                  25                  30

Met Trp Tyr Ala Lys Lys Gln Gly Gln Lys Asn Lys Gly Thr Gly Ser
            35                  40                  45

Gly Ala Gly Thr Gly Ser Gly Ala Gly Thr Gly Ser Gly Ala His Pro
    50                  55                  60

Gly His Leu Lys Gly Arg Glu Ile Gly Met Trp Tyr Ala Lys Lys Gln
65                  70                  75                  80

Gly Gln Lys Asn Lys Gly Thr Gly Ser Gly Ala Gly Thr Gly Ser Gly
                85                  90                  95

Ala Gly Thr Gly Ser Gly Ala His Pro Gly His Leu Lys Gly Arg Glu
            100                 105                 110

Ile Gly Met Trp Tyr Ala Lys Lys Gln Gly Gln Lys Asn Lys Gly Thr
        115                 120                 125

Gly Ser Gly Ala Asp Tyr Lys Asp His Asp Gly Asp Tyr Lys Asp His
    130                 135                 140

Asp Ile Asp Tyr Lys Asp Asp Asp Asp Lys
145                 150

<210> SEQ ID NO 7
<211> LENGTH: 195
<212> TYPE: PRT
<213> ORGANISM: Artificial Sequence
<220> FEATURE:
<223> OTHER INFORMATION: Fully synthetic

<400> SEQUENCE: 7

Met Gly Ser Ser His His His His His Ser Ser Gly Leu Val Pro
1               5                   10                  15

Arg Gly Ser His Met His Pro Gly His Leu Lys Gly Arg Glu Ile Gly
                20                  25                  30

Met Trp Tyr Ala Lys Lys Gln Gly Gln Lys Asn Lys Gly Thr Gly Ser
            35                  40                  45

Gly Ala Gly Thr Gly Ser Gly Ala Gly Thr Gly Ser Gly Ala His Pro
    50                  55                  60
```

Gly His Leu Lys Gly Arg Glu Ile Gly Met Trp Tyr Ala Lys Lys Gln
65                  70                  75                  80

Gly Gln Lys Asn Lys Gly Thr Gly Ser Gly Ala Gly Thr Gly Ser Gly
                85                  90                  95

Ala Gly Thr Gly Ser Gly Ala His Pro Gly His Leu Lys Gly Arg Glu
            100                 105                 110

Ile Gly Met Trp Tyr Ala Lys Lys Gln Gly Gln Lys Asn Lys Gly Thr
            115                 120                 125

Gly Ser Gly Ala Gly Thr Gly Ser Gly Ala Gly Thr Gly Ser Gly Ala
        130                 135                 140

His Pro Gly His Leu Lys Gly Arg Glu Ile Gly Met Trp Tyr Ala Lys
145                 150                 155                 160

Lys Gln Gly Gln Lys Asn Lys Gly Thr Gly Ser Gly Ala Asp Tyr Lys
                165                 170                 175

Asp His Asp Gly Asp Tyr Lys Asp His Asp Ile Asp Tyr Lys Asp Asp
            180                 185                 190

Asp Asp Lys
        195

<210> SEQ ID NO 8
<211> LENGTH: 23
<212> TYPE: DNA
<213> ORGANISM: Artificial Sequence
<220> FEATURE:
<223> OTHER INFORMATION: Fully synthetic

<400> SEQUENCE: 8
gggctgggct gggcttggcc ggg                                            23

<210> SEQ ID NO 9
<211> LENGTH: 25
<212> TYPE: DNA
<213> ORGANISM: Artificial Sequence
<220> FEATURE:
<223> OTHER INFORMATION: Fully synthetic

<400> SEQUENCE: 9
tattgttggt gggtgggtgg gttat                                          25

<210> SEQ ID NO 10
<211> LENGTH: 23
<212> TYPE: DNA
<213> ORGANISM: Artificial Sequence
<220> FEATURE:
<223> OTHER INFORMATION: Fully synthetic

<400> SEQUENCE: 10
gggccgggcc tggggcgcgc ggg                                            23

<210> SEQ ID NO 11
<211> LENGTH: 21
<212> TYPE: DNA
<213> ORGANISM: Artificial Sequence
<220> FEATURE:
<223> OTHER INFORMATION: Fully synthetic

<400> SEQUENCE: 11
ggggcggggc gcggggcggg g                                              21

<210> SEQ ID NO 12
<211> LENGTH: 30
<212> TYPE: DNA

```
<213> ORGANISM: Artificial Sequence
<220> FEATURE:
<223> OTHER INFORMATION: Fully synthetic

<400> SEQUENCE: 12
ggttagggtt agggttaggg ttagggttag                                30

<210> SEQ ID NO 13
<211> LENGTH: 19
<212> TYPE: RNA
<213> ORGANISM: Artificial Sequence
<220> FEATURE:
<223> OTHER INFORMATION: Fully synthetic

<400> SEQUENCE: 13
agggaggggc gggucuggg                                            19

<210> SEQ ID NO 14
<211> LENGTH: 19
<212> TYPE: DNA
<213> ORGANISM: Artificial Sequence
<220> FEATURE:
<223> OTHER INFORMATION: Fully synthetic

<400> SEQUENCE: 14
tgggcggagg gaagtggga                                            19

<210> SEQ ID NO 15
<211> LENGTH: 18
<212> TYPE: DNA
<213> ORGANISM: Artificial Sequence
<220> FEATURE:
<223> OTHER INFORMATION: Fully synthetic

<400> SEQUENCE: 15
ttagggttag ggttaggg                                             18

<210> SEQ ID NO 16
<211> LENGTH: 24
<212> TYPE: DNA
<213> ORGANISM: Artificial Sequence
<220> FEATURE:
<223> OTHER INFORMATION: Fully synthetic

<400> SEQUENCE: 16
tattgtggtg ggtgggtggg ttat                                      24

<210> SEQ ID NO 17
<211> LENGTH: 24
<212> TYPE: DNA
<213> ORGANISM: Artificial Sequence
<220> FEATURE:
<223> OTHER INFORMATION: Fully synthetic

<400> SEQUENCE: 17
ttgggttagg gttagggtta ggga                                      24

<210> SEQ ID NO 18
<211> LENGTH: 17
<212> TYPE: DNA
<213> ORGANISM: Artificial Sequence
<220> FEATURE:
<223> OTHER INFORMATION: Fully synthetic

<400> SEQUENCE: 18
agggtgggct gggaggt                                              17
```

```
<210> SEQ ID NO 19
<211> LENGTH: 21
<212> TYPE: RNA
<213> ORGANISM: Artificial Sequence
<220> FEATURE:
<223> OTHER INFORMATION: Fully synthetic

<400> SEQUENCE: 19
uuaggguuag gguuagggutu a                                              21

<210> SEQ ID NO 20
<211> LENGTH: 23
<212> TYPE: DNA
<213> ORGANISM: Artificial Sequence
<220> FEATURE:
<223> OTHER INFORMATION: Fully synthetic

<400> SEQUENCE: 20
gggcgcggga ggaaggggc ggg                                              23

<210> SEQ ID NO 21
<211> LENGTH: 19
<212> TYPE: DNA
<213> ORGANISM: Artificial Sequence
<220> FEATURE:
<223> OTHER INFORMATION: Fully synthetic

<400> SEQUENCE: 21
agggtgggga gggtgggga                                                  19

<210> SEQ ID NO 22
<211> LENGTH: 23
<212> TYPE: RNA
<213> ORGANISM: Artificial Sequence
<220> FEATURE:
<223> OTHER INFORMATION: Fully synthetic

<400> SEQUENCE: 22
uuaggguuag gguuaggguu agg                                             23

<210> SEQ ID NO 23
<211> LENGTH: 15
<212> TYPE: DNA
<213> ORGANISM: Artificial Sequence
<220> FEATURE:
<223> OTHER INFORMATION: Fully synthetic

<400> SEQUENCE: 23
ggttggtgtg gttgg                                                      15

<210> SEQ ID NO 24
<211> LENGTH: 24
<212> TYPE: DNA
<213> ORGANISM: Artificial Sequence
<220> FEATURE:
<223> OTHER INFORMATION: Fully synthetic

<400> SEQUENCE: 24
ggggccgggg ccggggccgg ggcc                                            24

<210> SEQ ID NO 25
<211> LENGTH: 22
<212> TYPE: DNA
<213> ORGANISM: Artificial Sequence
<220> FEATURE:
```

<223> OTHER INFORMATION: Fully synthetic

<400> SEQUENCE: 25
ggcgaggagg ggcgtggccg gc                                    22

<210> SEQ ID NO 26
<211> LENGTH: 27
<212> TYPE: DNA
<213> ORGANISM: Artificial Sequence
<220> FEATURE:
<223> OTHER INFORMATION: Fully synthetic

<400> SEQUENCE: 26
tcgggttgcg ggcgcagggc acgggcg                               27

<210> SEQ ID NO 27
<211> LENGTH: 45
<212> TYPE: DNA
<213> ORGANISM: Artificial Sequence
<220> FEATURE:
<223> OTHER INFORMATION: Fully synthetic

<400> SEQUENCE: 27
tcgcggcggc gcgcggcgat tgcgtttcgc cgcgcgccgc gccga           45

<210> SEQ ID NO 28
<211> LENGTH: 23
<212> TYPE: DNA
<213> ORGANISM: Artificial Sequence
<220> FEATURE:
<223> OTHER INFORMATION: Fully synthetic

<400> SEQUENCE: 28
cccgccccct tcctcccgcg ccc                                   23

<210> SEQ ID NO 29
<211> LENGTH: 19
<212> TYPE: DNA
<213> ORGANISM: Artificial Sequence
<220> FEATURE:
<223> OTHER INFORMATION: Fully synthetic

<400> SEQUENCE: 29
agcgtgggga gcgtgggga                                        19

<210> SEQ ID NO 30
<211> LENGTH: 54
<212> TYPE: DNA
<213> ORGANISM: Artificial Sequence
<220> FEATURE:
<223> OTHER INFORMATION: Fully synthetic

<400> SEQUENCE: 30
accctaaccc taaccctaac cctaattttt ttagggttag ggttagggtt aggg  54

<210> SEQ ID NO 31
<211> LENGTH: 22
<212> TYPE: DNA
<213> ORGANISM: Artificial Sequence
<220> FEATURE:
<223> OTHER INFORMATION: Fully synthetic

<400> SEQUENCE: 31
ttcacgcggg ctcggagtgg tt                                    22

```
<210> SEQ ID NO 32
<211> LENGTH: 22
<212> TYPE: DNA
<213> ORGANISM: Artificial Sequence
<220> FEATURE:
<223> OTHER INFORMATION: Fully synthetic

<400> SEQUENCE: 32
ccctaaccct aaccctaacc ct                                           22

<210> SEQ ID NO 33
<211> LENGTH: 18
<212> TYPE: RNA
<213> ORGANISM: Artificial Sequence
<220> FEATURE:
<223> OTHER INFORMATION: Fully synthetic

<400> SEQUENCE: 33
caguacagau cuguacug                                                18

<210> SEQ ID NO 34
<211> LENGTH: 24
<212> TYPE: RNA
<213> ORGANISM: Artificial Sequence
<220> FEATURE:
<223> OTHER INFORMATION: Fully synthetic

<400> SEQUENCE: 34
uuaccguuac cguuaccguu accg                                         24

<210> SEQ ID NO 35
<211> LENGTH: 55
<212> TYPE: DNA
<213> ORGANISM: Artificial Sequence
<220> FEATURE:
<223> OTHER INFORMATION: Fully synthetic

<400> SEQUENCE: 35
aagcagacag ctagtgaatt cagatagatg ggttgctcta caagcgtata actgt       55

<210> SEQ ID NO 36
<211> LENGTH: 55
<212> TYPE: DNA
<213> ORGANISM: Artificial Sequence
<220> FEATURE:
<223> OTHER INFORMATION: Fully synthetic

<400> SEQUENCE: 36
aagcagacag ctagtgaatt cagatagatg ggttgctcta caagcgtata actgt       55

<210> SEQ ID NO 37
<211> LENGTH: 21
<212> TYPE: RNA
<213> ORGANISM: Artificial Sequence
<220> FEATURE:
<223> OTHER INFORMATION: Fully synthetic

<400> SEQUENCE: 37
uacgcuugua gagcuugggu u                                            21

<210> SEQ ID NO 38
<211> LENGTH: 55
<212> TYPE: DNA
<213> ORGANISM: Artificial Sequence
<220> FEATURE:
<223> OTHER INFORMATION: Fully synthetic
```

<400> SEQUENCE: 38
aagcagacag ctagtgaatt cagatgggtg ggttgctcta caagcgtata actgt    55

<210> SEQ ID NO 39
<211> LENGTH: 25
<212> TYPE: RNA
<213> ORGANISM: Artificial Sequence
<220> FEATURE:
<223> OTHER INFORMATION: Fully synthetic

<400> SEQUENCE: 39
uacgcuugua gagcuugggu ggguu    25

<210> SEQ ID NO 40
<211> LENGTH: 55
<212> TYPE: DNA
<213> ORGANISM: Artificial Sequence
<220> FEATURE:
<223> OTHER INFORMATION: Fully synthetic

<400> SEQUENCE: 40
aagcagacag ctagtgaatt cgggtgggtg ggttgctcta caagcgtata actgt    55

<210> SEQ ID NO 41
<211> LENGTH: 21
<212> TYPE: DNA
<213> ORGANISM: Artificial Sequence
<220> FEATURE:
<223> OTHER INFORMATION: Fully synthetic

<400> SEQUENCE: 41
tgtccttctc ggctacacct g    21

<210> SEQ ID NO 42
<211> LENGTH: 22
<212> TYPE: DNA
<213> ORGANISM: Artificial Sequence
<220> FEATURE:
<223> OTHER INFORMATION: Fully synthetic

<400> SEQUENCE: 42
cacgcttcct ctaacatcaa cg    22

<210> SEQ ID NO 43
<211> LENGTH: 19
<212> TYPE: DNA
<213> ORGANISM: Artificial Sequence
<220> FEATURE:
<223> OTHER INFORMATION: Fully synthetic

<400> SEQUENCE: 43
gctcggcgat ggtaggcgt    19

<210> SEQ ID NO 44
<211> LENGTH: 18
<212> TYPE: DNA
<213> ORGANISM: Artificial Sequence
<220> FEATURE:
<223> OTHER INFORMATION: Fully synthetic

<400> SEQUENCE: 44
cccgcattca cgccccac    18

<210> SEQ ID NO 45
<211> LENGTH: 18

```
<212> TYPE: DNA
<213> ORGANISM: Artificial Sequence
<220> FEATURE:
<223> OTHER INFORMATION: Fully synthetic

<400> SEQUENCE: 45
tcaccgcagc acgccgag                                                    18

<210> SEQ ID NO 46
<211> LENGTH: 20
<212> TYPE: DNA
<213> ORGANISM: Artificial Sequence
<220> FEATURE:
<223> OTHER INFORMATION: Fully synthetic

<400> SEQUENCE: 46
cggagatgtg gccctggta                                                   20

<210> SEQ ID NO 47
<211> LENGTH: 20
<212> TYPE: DNA
<213> ORGANISM: Artificial Sequence
<220> FEATURE:
<223> OTHER INFORMATION: Fully synthetic

<400> SEQUENCE: 47
gaggtgggga cccgaataaa                                                  20

<210> SEQ ID NO 48
<211> LENGTH: 18
<212> TYPE: DNA
<213> ORGANISM: Artificial Sequence
<220> FEATURE:
<223> OTHER INFORMATION: Fully synthetic

<400> SEQUENCE: 48
tggccgagcc ttagagcc                                                    18

<210> SEQ ID NO 49
<211> LENGTH: 17
<212> TYPE: DNA
<213> ORGANISM: Artificial Sequence
<220> FEATURE:
<223> OTHER INFORMATION: Fully synthetic

<400> SEQUENCE: 49
cgccaacgcc acaacca                                                     17

<210> SEQ ID NO 50
<211> LENGTH: 17
<212> TYPE: DNA
<213> ORGANISM: Artificial Sequence
<220> FEATURE:
<223> OTHER INFORMATION: Fully synthetic

<400> SEQUENCE: 50
cggagggtcg catcgct                                                     17

<210> SEQ ID NO 51
<211> LENGTH: 17
<212> TYPE: DNA
<213> ORGANISM: Artificial Sequence
<220> FEATURE:
<223> OTHER INFORMATION: Fully synthetic

<400> SEQUENCE: 51
```

```
cccgccattt cggactg                                              17

<210> SEQ ID NO 52
<211> LENGTH: 18
<212> TYPE: DNA
<213> ORGANISM: Artificial Sequence
<220> FEATURE:
<223> OTHER INFORMATION: Fully synthetic

<400> SEQUENCE: 52
ggagccgctg agcctctg                                             18

<210> SEQ ID NO 53
<211> LENGTH: 17
<212> TYPE: DNA
<213> ORGANISM: Artificial Sequence
<220> FEATURE:
<223> OTHER INFORMATION: Fully synthetic

<400> SEQUENCE: 53
gatgcggggc gacagct                                              17

<210> SEQ ID NO 54
<211> LENGTH: 17
<212> TYPE: DNA
<213> ORGANISM: Artificial Sequence
<220> FEATURE:
<223> OTHER INFORMATION: Fully synthetic

<400> SEQUENCE: 54
agcggcgcaa ggaccac                                              17

<210> SEQ ID NO 55
<211> LENGTH: 19
<212> TYPE: DNA
<213> ORGANISM: Artificial Sequence
<220> FEATURE:
<223> OTHER INFORMATION: Fully synthetic

<400> SEQUENCE: 55
tccgccttcg ggatggtat                                            19

<210> SEQ ID NO 56
<211> LENGTH: 19
<212> TYPE: DNA
<213> ORGANISM: Artificial Sequence
<220> FEATURE:
<223> OTHER INFORMATION: Fully synthetic

<400> SEQUENCE: 56
gcgttgctgt gcgttcttc                                            19

<210> SEQ ID NO 57
<211> LENGTH: 24
<212> TYPE: DNA
<213> ORGANISM: Artificial Sequence
<220> FEATURE:
<223> OTHER INFORMATION: Fully synthetic

<400> SEQUENCE: 57
cttcctttgc ttctactccc agtt                                      24

<210> SEQ ID NO 58
<211> LENGTH: 19
<212> TYPE: DNA
<213> ORGANISM: Artificial Sequence
```

```
<220> FEATURE:
<223> OTHER INFORMATION: Fully synthetic

<400> SEQUENCE: 58
gcgcacttcc tcaacctcc                                                19

<210> SEQ ID NO 59
<211> LENGTH: 20
<212> TYPE: DNA
<213> ORGANISM: Artificial Sequence
<220> FEATURE:
<223> OTHER INFORMATION: Fully synthetic

<400> SEQUENCE: 59
cggtctcggg acacggacac                                               20

<210> SEQ ID NO 60
<211> LENGTH: 19
<212> TYPE: DNA
<213> ORGANISM: Artificial Sequence
<220> FEATURE:
<223> OTHER INFORMATION: Fully synthetic

<400> SEQUENCE: 60
ggacgtacgg ggcctggtg                                                19

<210> SEQ ID NO 61
<211> LENGTH: 20
<212> TYPE: DNA
<213> ORGANISM: Artificial Sequence
<220> FEATURE:
<223> OTHER INFORMATION: Fully synthetic

<400> SEQUENCE: 61
ccccaggatg tggagatgaa                                               20

<210> SEQ ID NO 62
<211> LENGTH: 17
<212> TYPE: DNA
<213> ORGANISM: Artificial Sequence
<220> FEATURE:
<223> OTHER INFORMATION: Fully synthetic

<400> SEQUENCE: 62
ccgtcttgcc gtctgcc                                                  17

<210> SEQ ID NO 63
<211> LENGTH: 22
<212> TYPE: DNA
<213> ORGANISM: Artificial Sequence
<220> FEATURE:
<223> OTHER INFORMATION: Fully synthetic

<400> SEQUENCE: 63
ctcaaccttt ggcctaaact cc                                            22

<210> SEQ ID NO 64
<211> LENGTH: 25
<212> TYPE: DNA
<213> ORGANISM: Artificial Sequence
<220> FEATURE:
<223> OTHER INFORMATION: Fully synthetic

<400> SEQUENCE: 64
ttggaggaac aagaggacta cagac                                         25
```

```
<210> SEQ ID NO 65
<211> LENGTH: 19
<212> TYPE: DNA
<213> ORGANISM: Artificial Sequence
<220> FEATURE:
<223> OTHER INFORMATION: Fully synthetic

<400> SEQUENCE: 65
ctctttgccg agctttccg                                                  19

<210> SEQ ID NO 66
<211> LENGTH: 18
<212> TYPE: DNA
<213> ORGANISM: Artificial Sequence
<220> FEATURE:
<223> OTHER INFORMATION: Fully synthetic

<400> SEQUENCE: 66
caccctctgc gctgttgc                                                   18

<210> SEQ ID NO 67
<211> LENGTH: 18
<212> TYPE: DNA
<213> ORGANISM: Artificial Sequence
<220> FEATURE:
<223> OTHER INFORMATION: Fully synthetic

<400> SEQUENCE: 67
tcgtcccgcg cacggatg                                                   18

<210> SEQ ID NO 68
<211> LENGTH: 21
<212> TYPE: DNA
<213> ORGANISM: Artificial Sequence
<220> FEATURE:
<223> OTHER INFORMATION: Fully synthetic

<400> SEQUENCE: 68
cccgacagca gctggaggag c                                               21

<210> SEQ ID NO 69
<211> LENGTH: 20
<212> TYPE: DNA
<213> ORGANISM: Artificial Sequence
<220> FEATURE:
<223> OTHER INFORMATION: Fully synthetic

<400> SEQUENCE: 69
gtatgggaga cggccaacaa                                                 20

<210> SEQ ID NO 70
<211> LENGTH: 20
<212> TYPE: DNA
<213> ORGANISM: Artificial Sequence
<220> FEATURE:
<223> OTHER INFORMATION: Fully synthetic

<400> SEQUENCE: 70
aggccagaca ggtgcaggta                                                 20

<210> SEQ ID NO 71
<211> LENGTH: 6
<212> TYPE: PRT
<213> ORGANISM: Artificial Sequence
<220> FEATURE:
<223> OTHER INFORMATION: Fully synthetic
```

```
<400> SEQUENCE: 71

Gly Thr Gly Ser Gly Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Fully synthetic

<400> SEQUENCE: 72

Pro Lys Lys Lys Arg Lys Val
1               5

<210> SEQ ID NO 73
<211> LENGTH: 20
<212> TYPE: DNA
<213> ORGANISM: Artificial Sequence
<220> FEATURE:
<223> OTHER INFORMATION: Fully synthetic

<400> SEQUENCE: 73
gtcaccaatc ctgtccctag                                              20

<210> SEQ ID NO 74
<211> LENGTH: 16
<212> TYPE: DNA
<213> ORGANISM: Artificial Sequence
<220> FEATURE:
<223> OTHER INFORMATION: Fully synthetic

<400> SEQUENCE: 74
gggtgggtgg gtgggt                                                  16
```

PEPTIDE PROBE FOR RECOGNITION OF G-QUADRUPLEX AND USE THEREOF IN DETECTION OF G-QUADRUPLEX IN CELL

CROSS-REFERENCE TO RELATED APPLICATIONS

Pursuant to 35 U.S.C. § 119 and the Paris Convention Treaty, this application claims foreign priority to Chinese Patent Application No. 202010413944.7 filed May 15, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

INCORPORATION-BY-REFERENCE OF SEQUENCE LISTING

This application contains a sequence listing, which has been submitted in ASCII text file via EFS-WEB and is incorporated herein by reference in its entirety. The ASCII text file, created on Sep. 8, 2021, is named SXCZ-00102-UUS_ST25.txt, and is 18,926 bytes in size.

BACKGROUND

The disclosure relates to the field of biological probes, and more particularly, to a polypeptide probe for detecting G-quadruplexes (G4s) and applications thereof in living cells.

G4s are four-stranded secondary structures formed by guanine-rich nucleic acids. Putative G-quadruplex forming sequences (PQSs) are abundant in the genomes of animal cells. The detection and quantitation of G4s in genomes with sequence identity are indispensable for G4 biology. Although G4s readily form in vitro in single-stranded nucleic acids, the situation in living cells is rather different. PQSs in chromosomes are constrained in long DNA duplexes where the two complementary DNA strands hybridize with each other. Chromosomes are further bound by proteins and compacted into a small volume to fit into a nucleus. The situation disfavors the formation of G4s. Recently, G4s have been detected in chemically fixed human cells by immunostaining or immunoprecipitation with G4 antibodies. Since the routinely used fixative, e.g. formaldehyde, ethanol, and acetic acid, can denature nucleic acid, there is a concern that G4s might form during fixing, permeabilizing, or staining cells. Therefore, whether G4s can form in living cells has been controversial and many biologists are still not fully convinced of their existence.

Antibodies are valuable probes for target recognition. However, they are not suitable for probing G4s in living cells because the reductive environment of the cytoplasm is not compatible with the formation of the disulfide bonds required for maintaining the tertiary structure of antibodies. The use of an antibody in living animal cells was extremely compromised, resulting in the identification of G4s only in telomeres in which long clusters of PQS are present. Native G4-interacting proteins are likely unsuitable either in that they normally process multi-functional domains such that they may interact with other proteins besides their DNA/RNA targets. There are chances that they are brought to DNA/RNA indirectly or subject to complex interactions, resulting in non-specificity or impeded recognition. Therefore, a more suitable protein probe is desired for detecting and quantitating G4s, and exploring their role in living cells.

SUMMARY

The disclosure provides a polypeptide probe for detecting G-quadruplexes (G4s). The polypeptide probe for detecting G-quadruplexes in the disclosure is named G4 probe (G4P).

The disclosure also provides a method for detecting G-quadruplexes of cells.

A polypeptide probe for detecting G4s in living cells comprises: from two to four G4-binding domains, and one or more linkers disposed between every two G4-binding domains. Each G4-binding domain comprises a specific motif comprising
a sequence of amino acids

PGHLKGREIGMWY.                    (SEQ ID NO: 1)

In a class of this embodiment, each G4-binding domain comprises 23 amino acids.

In a class of this embodiment, each G4-binding domain comprises a sequence of amino acids HPGHLKGREIGMWYAKKQGQKNK (SEQ ID NO: 2).

In a class of this embodiment, the G4-binding domains are 2 in number.

In a class of this embodiment, the one or more linkers comprise from two to four hexapeptides each comprising a sequence of amino acids GTGSGA (SEQ ID NO: 71).

In a class of this embodiment, the number of the hexapeptides is 3.

In a class of this embodiment, the polypeptide probe further comprises a protein tag located on a C-terminal of the polypeptide probe.

According to another aspect of the disclosure, provided is a method for detecting G-quadruplexes of a cell, the method comprising applying the polypeptide probe.

In a class of this embodiment, the G4s in the cell are detected by using chromatin immunoprecipitation-next-generation sequencing (ChIP-seq).

In a class of this embodiment, the cell is derived from a living human, mouse or chicken.

The following advantages are associated with the polypeptide probe of the disclosure in comparison with the prior art: the polypeptide probe possesses a simple structure thus minimizing the non-specific interaction with other proteins. The synergy of the G4-binding domains improves the affinity and selectivity thereof towards G4s. Therefore, the polypeptide probe has high specificity for detecting G4s, is compatible with the reducing environment in the living cells and is suitable for probing G4s.

DETAILED DESCRIPTION

Figure 1:
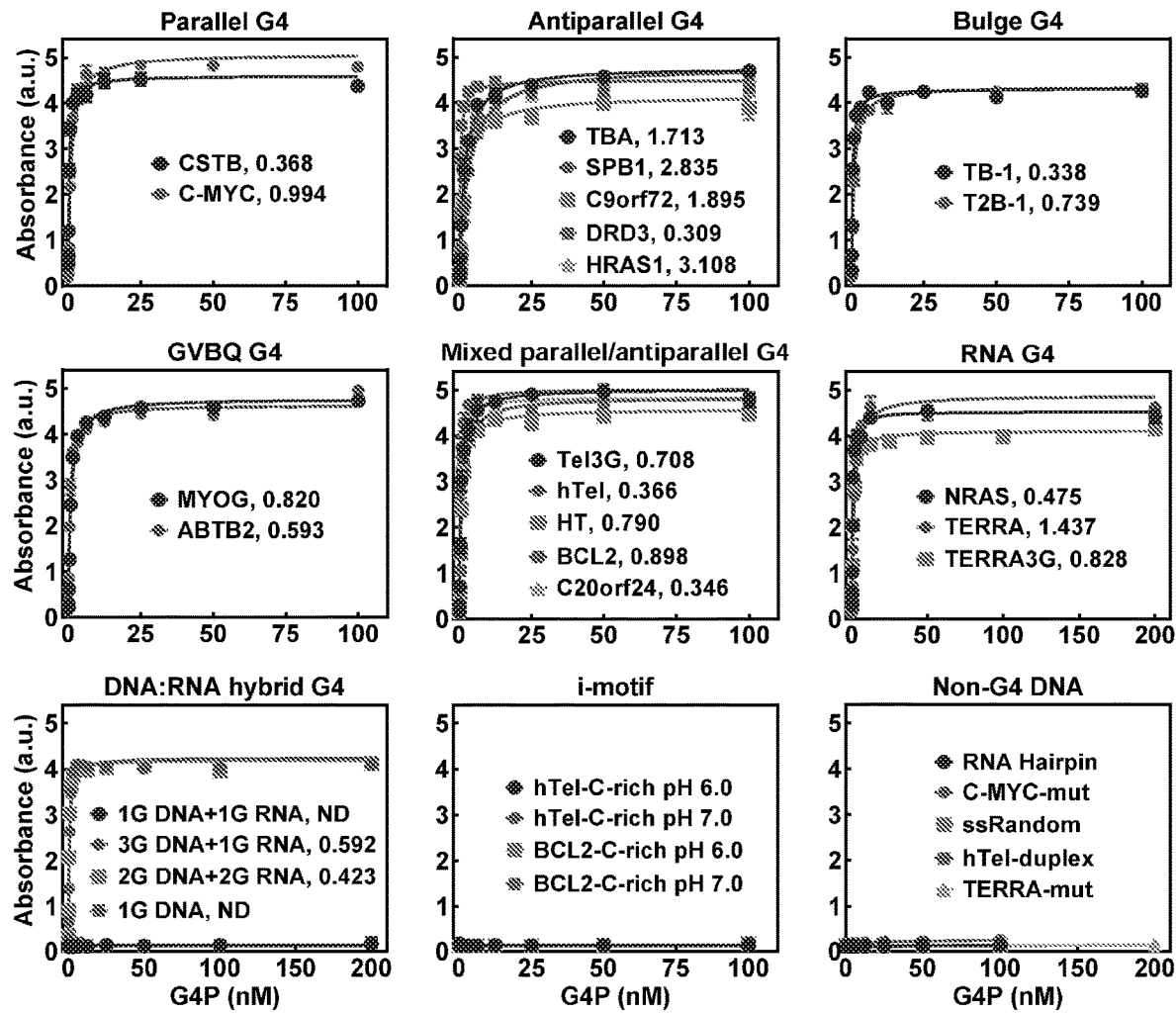
FIG. 1 is a graph of binding affinities of G4P to G4s of different types of conformations.

To further illustrate the disclosure, embodiments detailing a polypeptide probe are described below. It should be noted that the following embodiments are intended to describe and not to limit the disclosure.

The disclosure provides a polypeptide probe for detecting the G4s, comprising from two to four G4-binding domains, and one or more linkers disposed between every two the G4-binding domains. Each G4-binding domain comprises a specific motif comprising a sequence of amino acids PGHLKGREIGMWY (SEQ ID NO: 1). The specific motif functions as a major determinant for the affinity and specificity toward G4s in RHAU (RNA Helicase associated with AU-rich element). The polypeptide probe possesses a simple structure thus minimizing the non-specific interaction with other proteins. The synergy of the G4-binding domains improves the affinity and selectivity thereof towards G4s. Therefore, the polypeptide probe has high specificity for detecting G4s, is compatible with the reducing environment in the living cells and is suitable for probing G4s.

In certain embodiments, each G4-binding domain comprises 23 amino acids.

In certain embodiments, each G4-binding domain comprises a sequence of amino acids HPGHLKGREIGMWYAKKQGQKNK (SEQ ID NO: 2).

In certain embodiments, the number of the G4-binding domains is 2.

Therefore, the G4-binding domains in the polypeptide probe can clamp onto the two terminal G-quartets of a G4, resulting in a tighter binding because of synergy between two binding activities.

In certain embodiments, the one or more linkers contains from two to four hexapeptides each comprising a sequence GTGSGA (SEQ ID NO: 71). The one or more linkers are a short peptide of flexible amino acids.

In certain embodiments, the number of the hexapeptides is 3.

In certain embodiments, the polypeptide probe further comprises a protein tag located on the C-terminal of the polypeptide probe. The protein tag is 3 xFLAG for binding to the corresponding antibody.

The disclosure also provides a method for detecting G-quadruplexes of a cell, the method comprising applying the polypeptide probe.

In certain embodiments, the G4s in the cell are detected by using chromatin immunoprecipitation-next-generation sequencing (ChIP-seq).

In certain embodiments, the cell is derived from a living human, mouse or chicken.

The polypeptide probe can detect G4 formation in living cells, which enables evaluation of G4 formation on both genome-wide scale and locus of interest, making a contribution toward research on G4s biology.

A polypeptide probe was taken as an example of the disclosure to explain in detail about how G4s were detected in living cells. The polypeptide probe comprised two G4-binding domains, a linker comprising three hexapeptides (GTGSGA (SEQ ID NO: 71)), and a protein tag located on the C-terminal of the polypeptide probe. To facilitate the extraction and purification of the polypeptide probe, a protein tag HIS is located on the N-terminal of the polypeptide probe. The polypeptide probe of the disclosure comprises two G4-binding domains RHAU23. The gene sequence of G4P was shown in SEQ ID NO: 3, and the amino acid sequence of G4P was shown in SEQ ID NO: 4.

Example 1

Preparation of G4P

The gene sequence of G4P was inserted between the Nde I and EcoRI sites of pet28b vector, and introduced into a BL21-DE3 expression strain by plasmid transformation. The cells were incubated until the optical density (OD) reached 0.5, and 0.8 mM isopropylthio-galactoside (IPTG) was added and kept for 4 h at 37° C., followed by protein extraction and purification. The protein extraction was performed by using Capturem™ His-Tagged Purification Miniprep Kit (TAKARA). The purified protein was stored in a solution containing 20 mM Tris-HCl (pH 7.4), 150 mM NaCl, 0.1 mM EDTA, and 50% glycerol, and kept at −20° C.

Example 2

G4P Recognizes G4s with Specificity

In Example 2, enzyme-linked immunosorbent assay (ELISA) was used to detect the G4P binding ability of the probe to 21 canonical G4s with different sequences and several non-canonical G4s as reference sequences. 21 biotinylated nucleotides (Sequences in Table 1) were annealed in a buffer containing 10 mM Tris-HCl (pH 7.4), 150 mM KCl by heating to 95° C. and slowly cooling down to 20° C. The annealed oligonucleotides were immobilized on a streptavidin-coated plate (Sigma-Aldrich), followed by incubating with G4P or RHAU23 at the indicated concentrations. Detection of bound proteins used an anti-FLAG Mouse Monoclonal Antibody (Transgen Biotech, China), an HRP Conjugated Goat Anti-Mouse IgG (H+L) secondary antibody (Transgen Biotech, China), and a TMB ELISA Substrate (Transgen Biotech, China) according to the manufacturer's instructions. Absorbance was measured at 450 nm on a Multi-Plate Reader (Biotek, USA). Dissociation constants ($K_d$) were obtained from the binding curves. The standard error of mean values was calculated from three replicates.

TABLE 1

Kd of G4P to different G4 structures

| Name | Sequence (5' to 3') | Structure | Topology | Kd (nM) ± SD |
|---|---|---|---|---|
| DRD3 | GGGCTGGGCTGGGCTTGGCCGGG (SEQ ID NO: 8) | G4 | Antiparallel | 0.31 ± 0.03 |
| T2B-1 | TATTGTTGGTGGGTGGGTGGGTTAT (SEQ ID NO: 9) | G4, Bulge | Parallel | 0.34 ± 0.02 |

TABLE 1-continued

Kd of G4P to different G4 structures

| Name | Sequence (5' to 3') | Structure | Topology | Kd (nM) ± SD |
|---|---|---|---|---|
| C20orf24 | GGGCCGGGCCTGGGCGCGCGGG (SEQ ID NO: 10) | G4 | Mixed parallel and antiparallel | 0.35 ± 0.03 |
| CSTB | GGGGCGGGGCGCGGGGCGGGG (SEQ ID NO: 11) | G4 | Parallel | 0.37 ± 0.03 |
| hTel | GG(TTAGGG)4TTAG (SEQ ID NO: 12) | G4 | Mixed parallel and antiparallel | 0.37 ± 0.03 |
| 2G DNA + 2G RNA | See rows at bottom | 2/2 DNA/RNA Hybrid G4 | Parallel | 0.42 ± 0.06 |
| NRAS RNA | AGGGAGGGGCGGGUCUGGG (SEQ ID NO: 13) | G4 | ND | 0.48 ± 0.03 |
| ABTB2 | TGGGCGGAGGGAAGTGGGA (SEQ ID NO: 14) | G4, GVBQ | ND | 0.59 ± 0.04 |
| 3G DNA + 1G RNA | See rows at bottom | 3/1 DNA/RNA Hybrid G4 | Parallel | 0.59 ± 0.10 |
| hTel-3G | TTAGGGTTAGGGTTAGGG (SEQ ID NO: 15) | intermolecular G4 | Mixed parallel and antiparallel | 0.71 ± 0.05 |
| TB-1 | TATTGTGGTGGGTGGGTGGGTTAT (SEQ ID NO: 16) | G4, Bulge | ND | 0.74 ± 0.05 |
| HT | TTGGGTTAGGGTTAGGGTTAGGGA (SEQ ID NO: 17) | G4 | Mixed parallel and antiparallel | 0.79 ± 0.05 |
| MYOG | AGGGTGGGCTGGGAGGT (SEQ ID NO: 18) | G4, GVBQ | ND | 0.82 ± 0.05 |
| TERRA3G | UUAGGGUUAGGGUUAGGGUUA (SEQ ID NO: 19) | intermolecular G4 | Parallel | 0.83 ± 0.05 |
| Bcl2 | GGGCGCGGGAGGAAGGGGGCGGG (SEQ ID NO: 20) | G4 | Mixed parallel and antiparallel | 0.9 ± 0.08 |
| c-MYC | AGGGTGGGGAGGGTGGGGA (SEQ ID NO: 21) | G4 | Parallel | 0.99 ± 0.1 |
| TERRA | UUAGGGUUAGGGUUAGGGUUAGGG (SEQ ID NO: 22) | G4 | Parallel | 1.437 ± 0.11 |
| TBA | GGTTGGTGTGGTTGG (SEQ ID NO: 23) | G4 | Antiparallel | 1.71 ± 0.1 |
| C9orf72 | GGGGCCGGGGCCGGGGCGGGGCC (SEQ ID NO: 24) | G4 | Antiparallel | 1.89 ± 0.21 |
| SPB1 | GGCGAGGAGGGGCGTGGCCGGC (SEQ ID NO: 25) | G4 | Antiparallel | 2.83 ± 0.15 |
| HRAS1 | TCGGGTTGCGGGCGCAGGGCACGGGCG (SEQ ID NO: 26) | G4 | Antiparallel | 3.11 ± 0.25 |
| DNA Hairpin | TCGCGGCGGCGCGCGGCGATTGCGTTTCGCCGCGCGCCGCGCCGA (SEQ ID NO: 27) | DNA stem loop | NA (not applicable) | UD (hard to detect) |
| Bcl2-C-rich | CCCGCCCCCTTCCTCCCGCGCCC (SEQ ID NO: 28) | i-motif | NA | UD |

TABLE 1-continued

Kd of G4P to different G4 structures

| Name | Sequence (5' to 3') | Structure | Topology | Kd (nM) ± SD |
|---|---|---|---|---|
| c-MYC-M | AGCGTGGGGAGCGTGGGGA (SEQ ID NO: 29) | ssDNA | NA | UD |
| hTel-Duplaex 4 | A(CCCTAA)4T5(TTAGGG) (SEQ ID NO: 30) | dsDNA | NA | UD |
| ssDNA | TTCACGCGGGCTCGGAGTGGTT (SEQ ID NO: 31) | ssDNA | NA | UD |
| hTel-C-rich | CCCTAACCCTAACCCTAACCCT (SEQ ID NO: 32) | i-motif | NA | UD |
| RNA Hairpin | CAGUACAGAUCUGUACUG (SEQ ID NO: 33) | RNA stem loop | NA | UD |
| TERRA-mut | UUACCGUUACCGUUACCGUUACCG (SEQ ID NO: 34) | ssRNA | NA | UD |
| 1G DNA | AAGCAGACAGCTAGTGAATTCAGATAGATGGGTTGCTCTACAAGCGTATAACTGT (SEQ ID NO: 35) | ssDNA | NA | UD |
| 1G DNA + 1G RNA | See below | | DNA:RNA hybrid duplex | NA UD |
| 1G DNA | AAGCAGACAGCTAGTGAATTCAGATAGATGGGTTGCTCTACAAGCGTATAACTGT (SEQ ID NO: 36) | ND (not determined) | | |
| 1G RNA | UACGCUUGUAGAGCUUGGGUU (SEQ ID NO: 37) | ND | | |
| 2G DNA | AAGCAGACAGCTAGTGAATTCAGATGGGTGGGTTGCTCTACAAGCGTATAACTGT (SEQ ID NO: 38) | ND | | |
| 2G RNA | UACGCUUGUAGAGCUUGGGUGGGUU (SEQ ID NO: 39) | ND | | |
| 3G DNA | AAGCAGACAGCTAGTGAATTCGGGTGGGTGGGTTGCTCTACAAGCGTATAACTGT (SEQ ID NO: 40) | ND | | |

FIG. 1 is a graph of binding affinity of G4P to G4s of different types or configurations, where abscissa represents the probe concentration and ordinate represents the absorbance.

Referring to FIG. 1 and Table 1, in the 21 G4s that included canonical DNA and RNA G4s, intermolecular DNA G4s, DNA:RNA hybrid G4s, G-vacancy-bearing G4s (GVBQs) and bulge G4s, the G4P showed a $K_d$ of sub-nM to 16 G4s and of 1-3 nM to 5 G4s. The $K_d$ values for these G4s ranged from 0.31-3.11 nM within one order of magnitude. The polypeptide probe G4P had a high affinity for the canonical G4P, and other forms of G4s were also captured. Therefore, the following were searched for PQSs of the three well-characterized non-canonical G4s, i.e. G4s with one loop of 8-15 nucleotides (4GL15), G-vacancy-bearing G4s (GVBQ), G4 with a bulge (Bulge), respectively. The G4P had no binding to the non-G4 DNAs or RNAs, including single-stranded DNA (ssDNA), RNA hairpin, DNA: RNA heteroduplex, and i-motif. Analysis of the result indicated that the polypeptide probe G4P of the disclosure can bind canonical and non-canonical G4s with high affinity and specificity.

Figure 2:
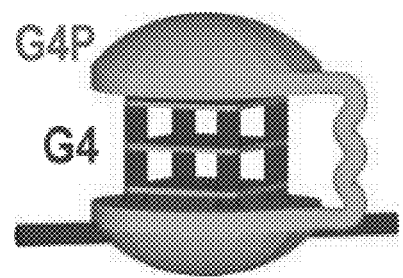
FIG. 2 shows a schematic drawing of clamping-binding of a G4 by a G4P.

FIG. 2 showed a clamping-binding of a G4 by a G4P. Each of the two terminal guanine quartets (G-quartet) of a G4 can bind the RHAU23. Therefore, the two RHAU23s in the G4P can clamp onto the two terminal G-quartets of the G4, resulting in a tighter binding because of synergy between two binding activities.

Figure 3:
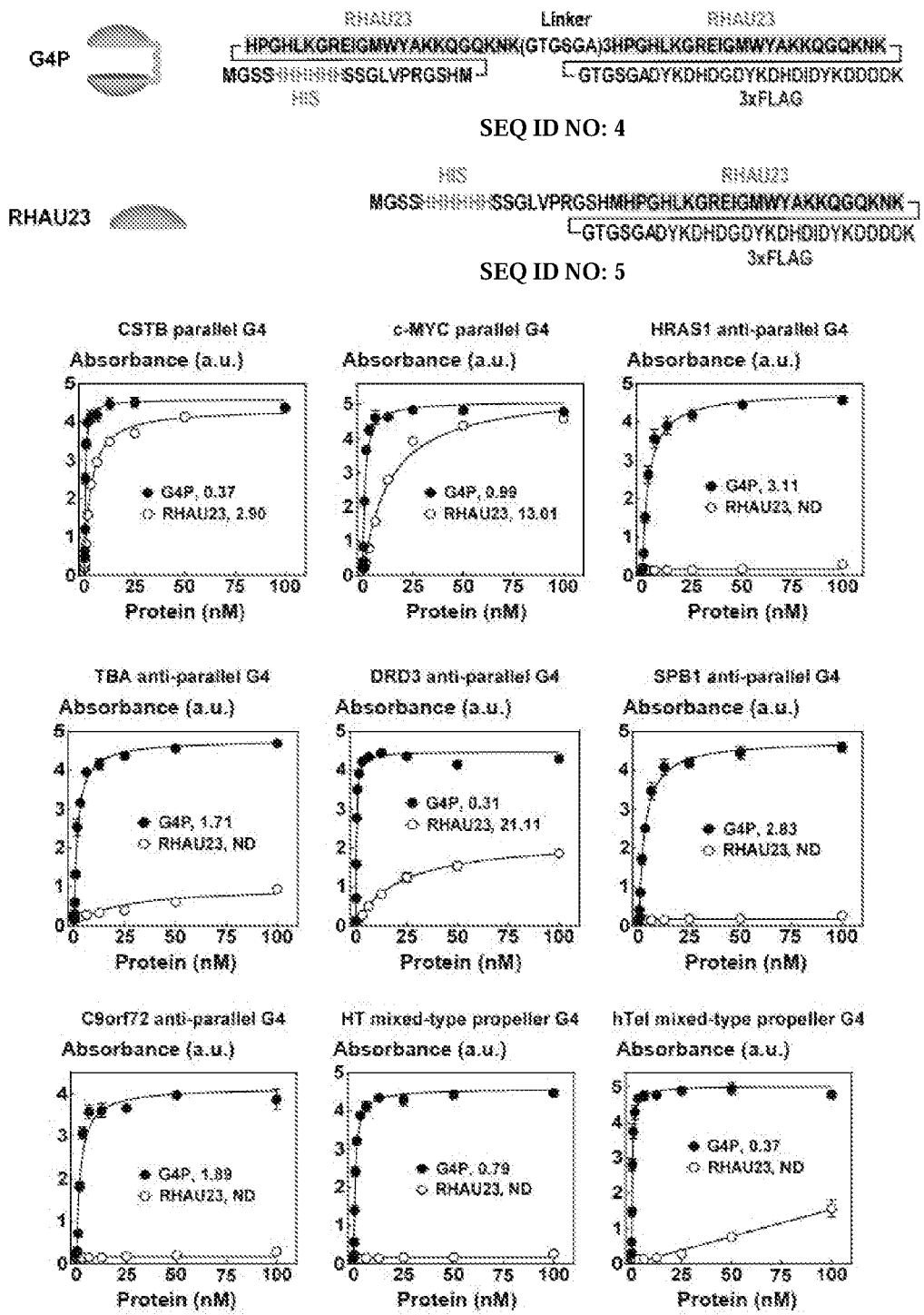
FIG. 3 is a comparison of G4 binding affinity between G4P and the monomeric RHAU23.
Figure 4:
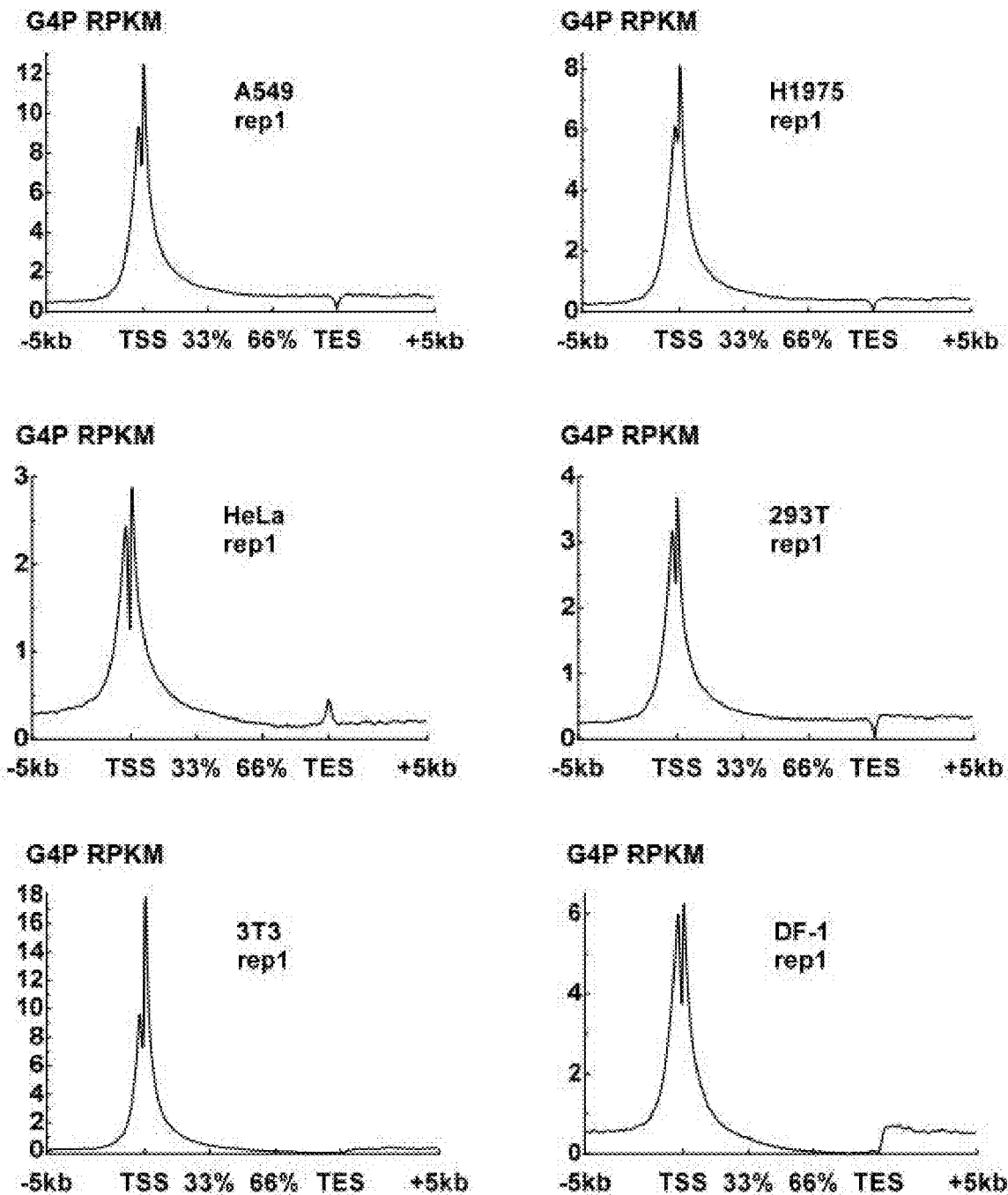
FIG. 4 shows the profiles of G4 reads across RefSeq genes in A549, 293T, HeLa-S3, NCI-H1975, mouse 3T3, and chicken DF-1 cells.
Figure 5:
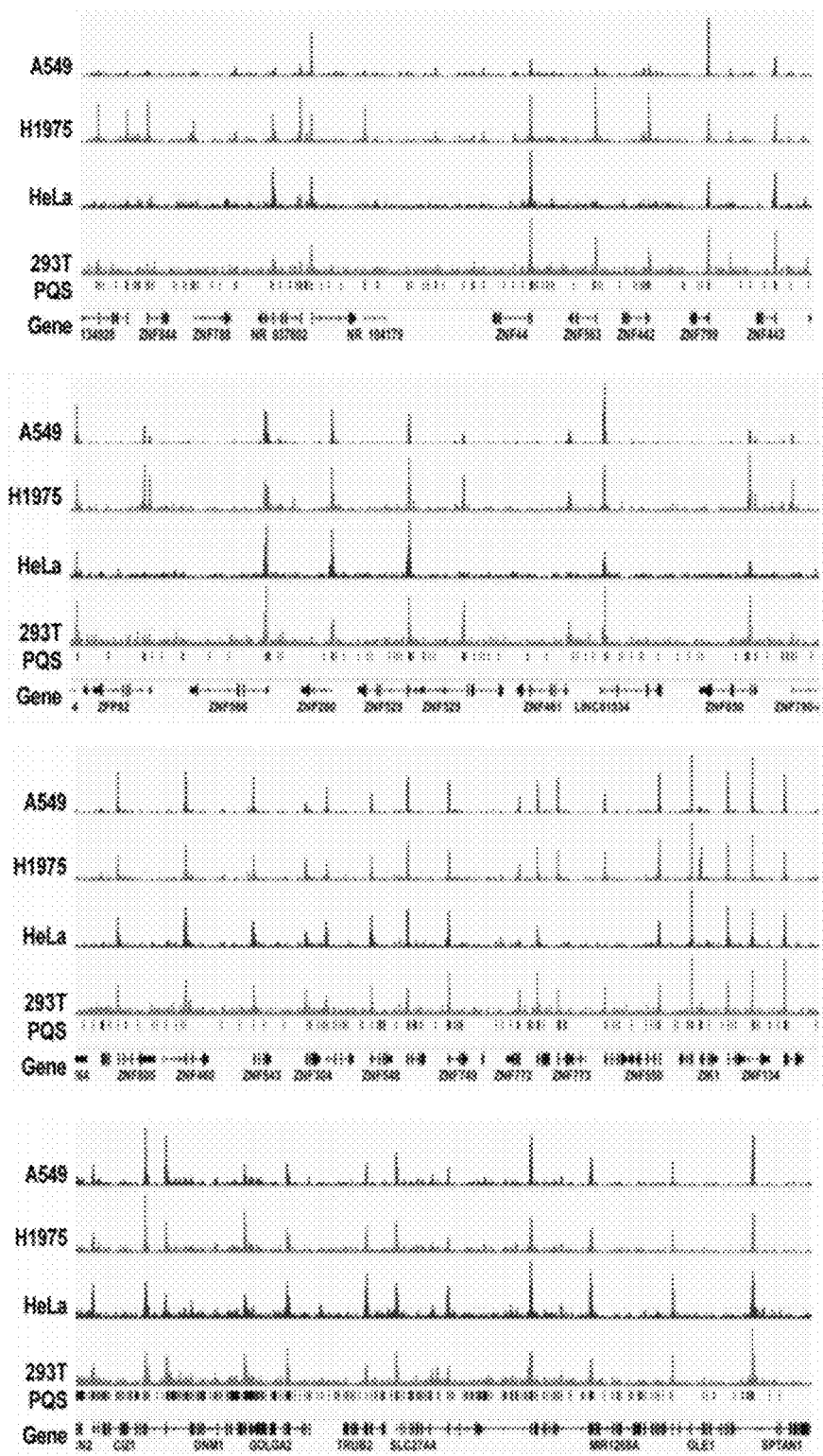
FIG. 5 is an example of G4 formation in human cells depicted by G4-ChIP.
Figure 6:
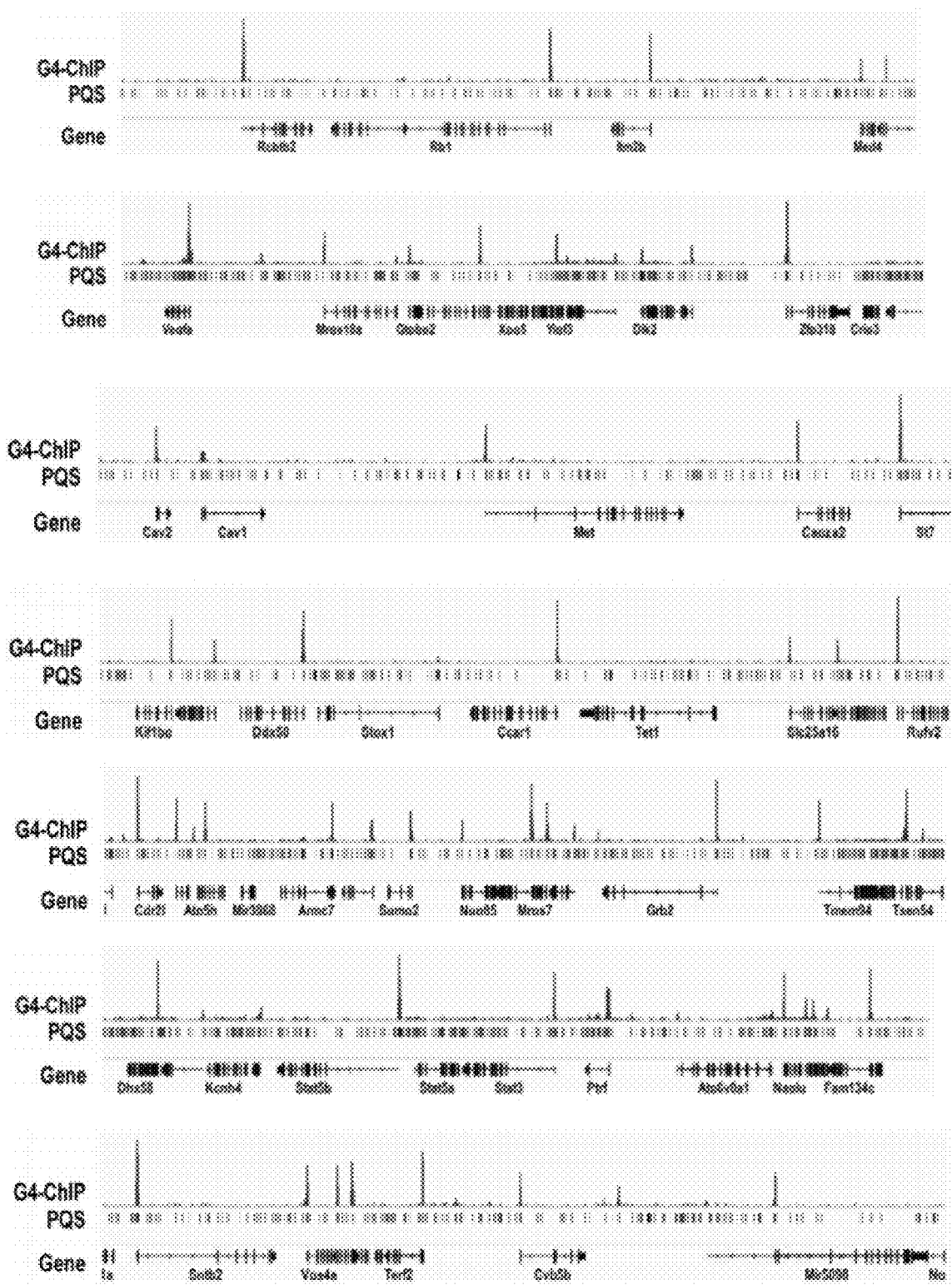
FIG. 6 is an example of G4 formation in mouse 3T3 cells depicted by G4-ChIP.
Figure 7:
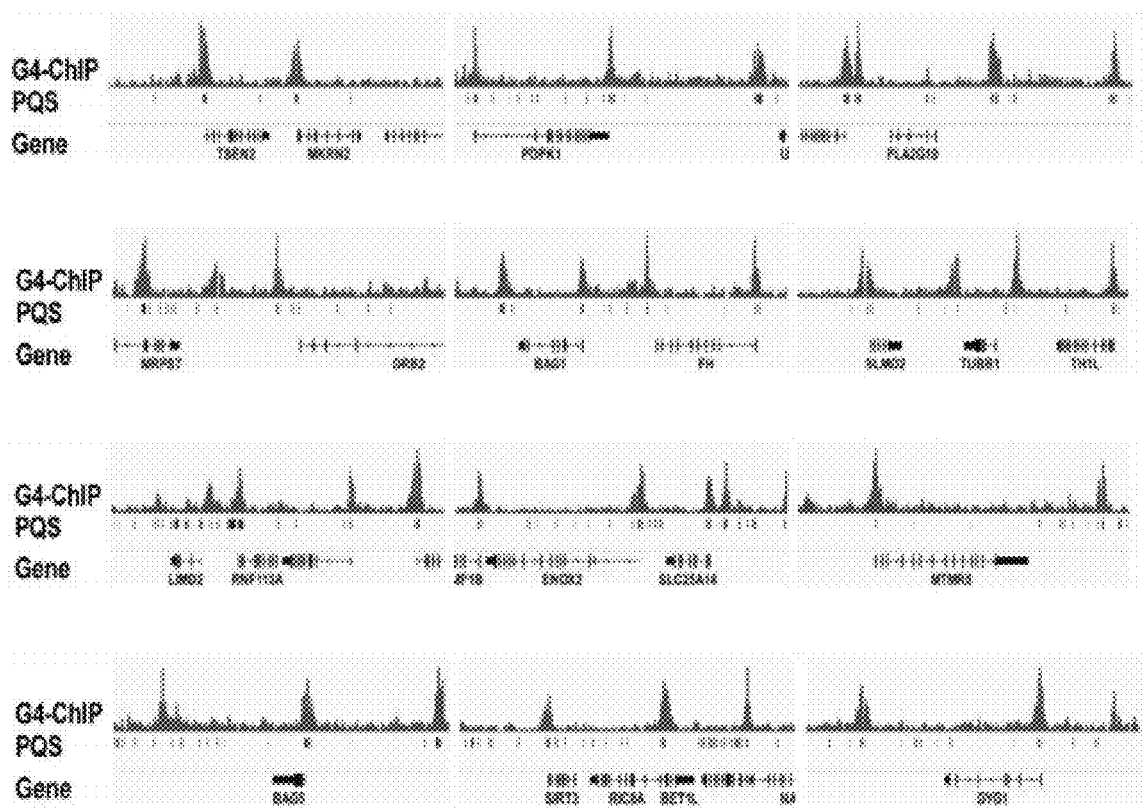
FIG. 7 is an example of G4 formation in chicken DF-1 cells depicted by G4-ChIP.

A comparison of G4 binding affinity between G4P and a monomeric RHAU23 was further performed. A G4P comprising only one G4-binding domain was termed monomeric RHAU23. FIG. 3 showed a comparison of G4 binding affinity between G4P and the monomeric RHAU23; where abscissa represents the probe concentration and ordinate represents the absorbance. As shown in FIG. 3, unlike the RHAU23 which only binds parallel, but not nonparallel G4s, the G4P showed almost no discrimination between the parallel and nonparallel G4. And the $K_d$ of the G4P to the parallel G4s increased by 10 folds or much more in comparison with the monomeric RHAU23.

Example 3

G4P Recognizes G4s in Living Cells

To capture G4s in living cells, the G4P were expressed in the cultured human A549 cells by transfection with a plasmid and performed G4-ChIP. The G4-ChIP libraries were sequenced and reads were mapped to the corresponding genomes.

The detailed description is as follows:

Plasmid Construction for G4P-ChIP:

The DNA encoding G4P was synthesized by Generay Biotechnology (Shanghai, China), and inserted between the Nde I and EcoRI sites of pIRES2-EGFP vector to obtain pG4P-IRES2-EGFP. The DNA fragment containing nuclear localization signal (NLS: PKKKRKV (SEQ ID NO: 72)) of the SV40 large antigen was synthesized by Sangon (Shanghai, China), and inserted into the Nde I site of the pG4P-IRES2-EGFP to obtain a plasmid pNLS-G4P-IRES2-EGFP.

The DNA fragment expressing NLS-G4P and eGFP was amplified from the pNLS-G4P-IRES2-EGFP and inserted into the AAVS1 donor plasmid between the Spe I and Sal I sites. The AAVS1 loci specific guide RNA sequence (5'-GTCACCAATCCTGTCCCTAG-3') (SEQ ID NO: 73) was designed by the online CRISPR tool (crispr.mit.edu.) and inserted into the PX330 plasmid between two Bbs I sites.

Cell lines: A549, NCI-H1975, 293T, HeLa-S3, 3T3, and DF-1 cells were kindly provided by Stem Cell Bank, Chinese Academy of Sciences.

Cell culture conditions: the cells were grown in DMEM comprising 10% Fetal Bovine Serum (FBS), 100 U/mL penicillin, and 0.1 mg/mL Streptomycin.

Transient transfection and gene knock-in:

For transient transfection, the cells were cultured in 15 cm dishes to 70-80% confluence and transfected with 30 μg of pNLS-G4P-IRES2-EGFP using lipofectamine 3000 (Thermo Scientific) according to the manufacturer's instructions. The cells were cultured for an additional 24 hours before harvesting.

For gene knock-in, AAVS1 donor and PX330 plasmid containing G4P and AAVS1 gRNA were co-transfected into 293T cells using lipofectamine 2000 (Thermo Scientific). After 24 hours, GFP positive single cell was sorted by a flow cytometer (MoFlo XDP, Beckman) into a 96-well plate. The cells were cultured for two weeks and the cell lines with a stable expression of G4P were verified by PCR.

G4-ChIP and DNA library construction:

Approximately 0.5-1×10$^7$ transiently or stably transfected cells expressing G4P were crosslinked with 1% formaldehyde for 20 min at room temperature. Fixation was quenched by 0.125 M glycine for 15 min. The fixed cells were washed twice with PBS, suspended in NP-40 buffer (10 mM Tris-HCl pH 7.4, 150 mM NaCl, 0.5% NP-40 and 2 mM AEBSF) and incubated on ice for 10 min. After centrifugation at 800×g for 5 min, the cell pellet was resuspended in a CHAPS buffer (20 mM Tris-HCl pH 7.4, 0.5 mM EGTA, 50 mM NaCl, 0.5% CHAPS, 10% glycerol and 2 mM AEBSF). The suspension was incubated on ice for 30 min, and centrifuged at 800×g for 5 min. The pellet was resuspended in 1 ml of 1×dsDNase digestion buffer supplied with 50 μl of dsDNase (Invitrogen, EN0771) and incubated at 37° C. for 20 min with constant agitation. A final concentration of 20 mM EDTA was added to terminate the reaction. The nuclei were pelleted by centrifugation at 15,000×g at 4° C. and the supernatant was incubated on ice. The nuclei pellet was resuspended in 500 μl of 1 wash buffer (150 mM NaCl, 10 mM Tris-HCl, pH 7.4, 0.1 mM EDTA, 0.5% Triton X-100) and sonicated for 30-60 seconds in an ice-cold water bath. After centrifugation at 15000×g for 5 min, the supernatant was collected and combined with the supernatant from the previous step.

For library preparation, 50 μl of anti-FLAG M2 magnetic beads (Sigma-Aldrich) were washed with washing buffer (10 mM Tris-HCl, pH 8.0, 150 mM NaCl, and 0.5% Triton X-100) and blocked in the same buffer containing 75 μg/ml single-stranded sperm DNA and 1 mg/ml BSA. 1% chromatin fragment was saved as input and the remaining was incubated with blocked anti-FLAG magnetic beads in rotation at 4° C. for 3 hrs. Beads were sequentially washed ten times with washing buffer and transferred to new tubes three times. The chromatin was eluted with 300 μg/ml 3×FLAG peptide (Sigma-Aldrich) and incubated at 4° C. for 1 hour. The eluted chromatin and the input samples were incubated with proteinase K at 65° C. overnight. After sequential RNase A and proteinase K digestion, DNA fragment was cleaned by extraction with phenol: chloroform: isoamyl alcohol, followed by ethanol precipitation. Libraries were constructed from the recovered DNA fragment using the NEBNext Ultra II DNA LibraryPrep Kit from Illumina (NEB) according to the manufacturer's instructions. The next-generation sequencing was performed with Illumina HiSeq X Ten by Genewiz (Suzhou, China).

ChIP-qPCR:

TABLE 2

| ChIP-qPCR primers | |
|---|---|
| Gene | Sequence: 5' to 3' |
| ADAR | TGTCCTTCTCGGCTACACCTG (SEQ ID NO: 41) |
|  | CACGCTTCCTCTAACATCAACG (SEQ ID NO: 42) |
| CBFA2T2 | GCTCGGCGATGGTAGGCGT (SEQ ID NO: 43) |
|  | CCCGCATTCACGCCCCAC (SEQ ID NO: 44) |
| CD47 | TCACCGCAGCACGCCGAG (SEQ ID NO: 45) |
|  | CGGAGATGTGGCCCCTGGTA (SEQ ID NO: 46) |
| EGFR | GAGGTGGGGACCCGAATAAA (SEQ ID NO: 47) |
|  | TGGCCGAGCCTTAGAGCC (SEQ ID NO: 48) |
|  | CGCCAACGCCACAACCA (SEQ ID NO: 49) |
|  | CGGAGGGTCGCATCGCT (SEQ ID NO: 50) |
| KRAS | CCCGCCATTTCGGACTG (SEQ ID NO: 51) |
|  | GGAGCCGCTGAGCCTCTG (SEQ ID NO: 52) |
| MET | GATGCGGGGCGACAGCT (SEQ ID NO: 53) |
|  | AGCGGCGCAAGGACCAC (SEQ ID NO: 54) |
| PIK3CA | TCCGCCTTCGGGATGGTAT (SEQ ID NO: 55) |
|  | GCGTTGCTGTGCGTTCTTC (SEQ ID NO: 56) |
|  | CTTCCTTTGCTTCTACTCCCAGTT (SEQ ID NO: 57) |
|  | GCGCACTTCCTCAACCTCC (SEQ ID NO: 58) |
| PLAA | CGGTCTCGGGACACGGACAC (SEQ ID NO: 59) |
|  | GGACGTACGGGGCCTGGTG (SEQ ID NO: 60) |
| PSMD3 | CCCCAGGATGTGGAGATGAA (SEQ ID NO: 61) |
|  | CCGTCTTGCCGTCTGCC (SEQ ID NO: 62) |
|  | CTCAACCTTTGGCCTAAACTCC (SEQ ID NO: 63) |
|  | TTGGAGGAACAAGAGGACTACAGAC (SEQ ID NO: 64) |
| TERF1 | CTCTTTGCCGAGCTTTCCG (SEQ ID NO: 65) |
|  | CACCCTCTGCGCTGTTGC (SEQ ID NO: 66) |
| TUSC1 | TCGTCCCGCGCACGGATG (SEQ ID NO: 67) |
|  | CCCGACAGCAGCTGGAGGAGC (SEQ ID NO: 68) |

TABLE 2-continued

ChIP-qPCR primers

| Gene | Sequence: 5' to 3' |
|---|---|
| WDR43 | GTATGGGAGACGGCCAACAA (SEQ ID NO: 69) |
| | AGGCCAGACAGGTGCAGGTA (SEQ ID NO: 70) | qPCR reaction was performed using the GoTaq qPCR Master Mix (Promega) and qTOWER 2.2. The cycling condition was 95° C. for 20 s followed by 45 cycles of 30 s at 95° C. and 30 s at 60° C. The enrichment of the genomic locus in the chip sample relative to the input was calculated using double delta Ct analysis with a PQS negative region as references.

ChIP-Seq data analysis:

Clean paired-end sequencing data were mapped to the human genome using Bowtie2. Mapped reads were written to bam files after being filtered by samtools view to remove poor alignments with the parameter—q 20 and by samtools rmdup to remove duplicates. Reads bam files were processed by the deeptools bamCompare to produce bigwig coverage file in ratio or subtract mode. Profiles and heatmaps of reads were generated from the bigwig files using the deeptools computeMatrix followed by plotProfile and plotHeatmap, respectively, with region bed files derived from the NCBI RefSeq bed file downloaded from the UCSC website (genome.ucsc.edu). Coordinate duplicates in the bed files were removed. Peaks of reads enrichment were identified with the macs2 using—qvalue 0.001, —keep-dup 1, and default values for the other parameters. ChIP-Seq data from public repositories were downloaded from the GEO (www.ncbi.nlm.nih.gov/geo/) or Encode (www.encodeproject.org/) database and processed as described above.

The disclosure used the above methods to detect G4s in living cells derived from human A549, NCI-H1975, HeLa-S3, 293T, and mouse 3T3, and chicken DF-1. The results were shown in FIGS. 4-7.

Figure 8:
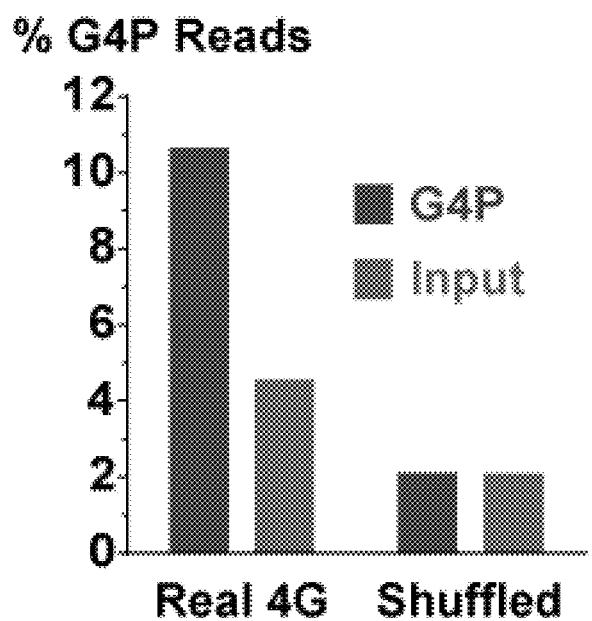
FIG. 8 is a graph of G4P reads at 4G PQSs as percent of total reads mapped to the genome.
Figure 9A:
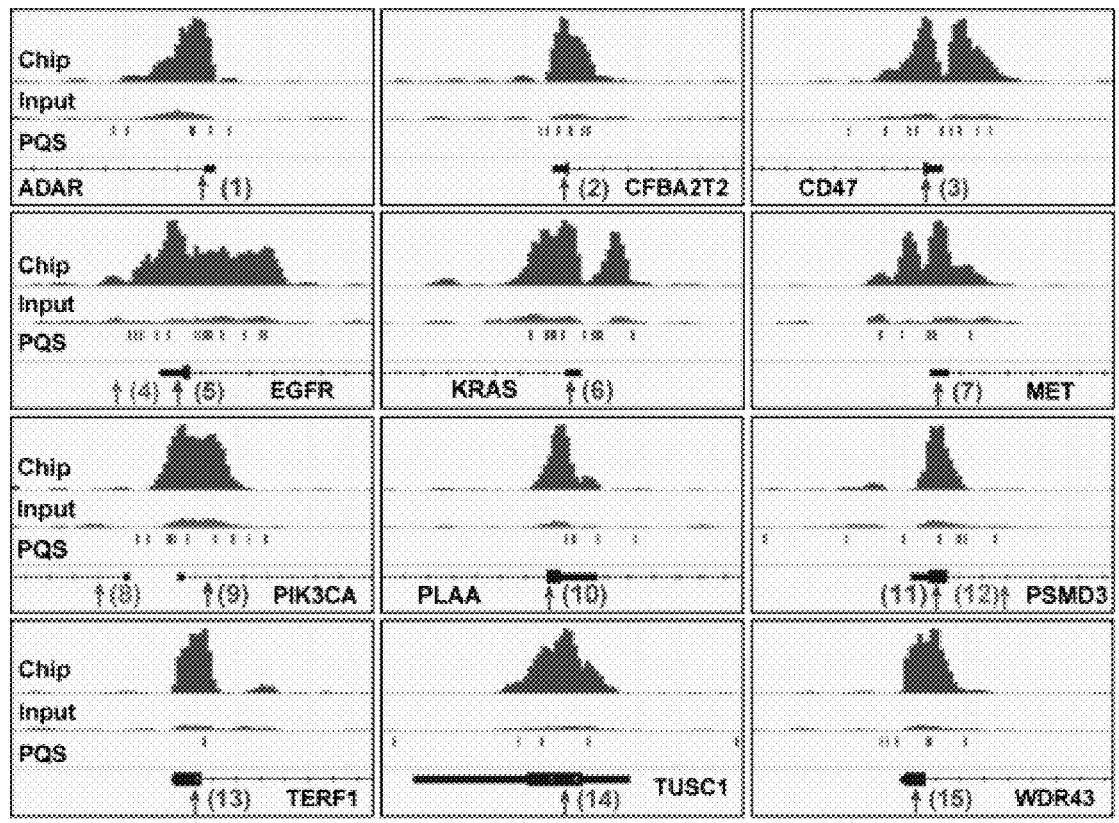
FIG. 9A shows G4P enrichment by ChIP-qPCR, where qPCR regions are indicated by arrowheads.
Figure 9B:
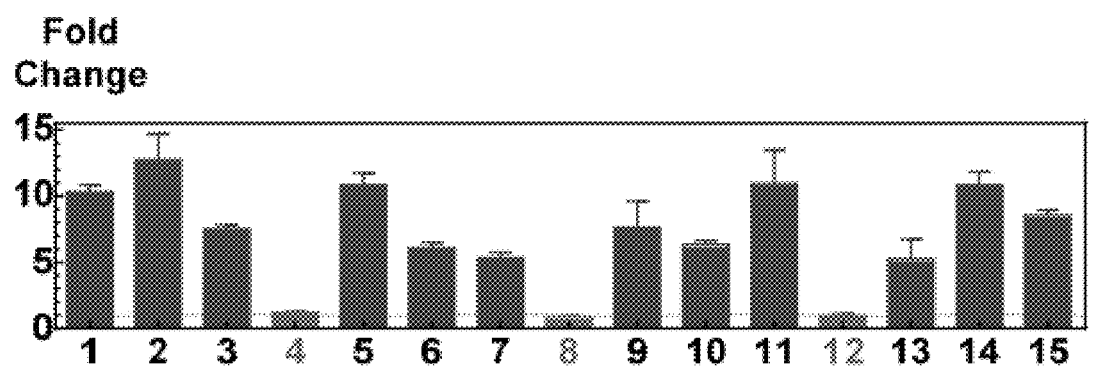
FIG. 9B is a verification of G4P enrichment by ChIP-qPCR. Enrichment of G4P at indicated qPCR regions expressed as means of duplicate with range.

The ability of the G4P to recognize G4s in cells was first demonstrated by the enrichment of G4P reads mapped to the canonical PQS motifs. To distinguish this type of PQSs from the non-canonical ones, they were termed 4G PQSs. The enrichment disappeared when the coordinates of the 4G PQSs were shuffled and the reads at these fake motifs counted. This result indicated a specific recognition of G4s at the 4G PQSs. The recognition of G4s was next illustrated by a peak when the G4P reads were profiled around the center of the 4G PQSs. FIG. 8 was a graph of G4P reads at 4G PQSs as % of total reads mapped to the genome. The recognition of G4s by the G4P was further verified by ChIP-qPCR (FIGS. 9A and 9B). Collectively, these results revealed a specific binding of G4P to the G4s at the 4G PQSs in the living cells.

The G4P of the disclosure had a much smaller size, higher affinities, and little discrimination to the different forms of G4s. With the removal of >90% of the amino acid residues from the original RHAU, the G4P was unlikely to interact with other proteins, therefore, ensuring direct target recognition and specificity. Most importantly, the G4P of the disclosure overcame the problem of disulfide bonds associated with antibodies such that the G4P is applicable in living cells.

Example 4

G4s binds the protein comprising 1-4 binding domains RHAU23, respectively.

The protein comprising only one binding domain RHAU23 was termed monomer, with a sequence of amino acids as shown in SEQ ID NO: 5. The protein comprising three binding domains RHAU23s were termed triplex, with a sequence of amino acids as shown in SEQ ID NO: 6. The protein comprising four binding domains RHAU23s were termed tetrad, with a sequence of amino acids as shown in SEQ ID NO: 7.

The gene sequences of monomer, G4P, triplex, and tetrad were respectively inserted between the Nde I and EcoRI sites of pet28b vector, and introduced into a BL21-DE3 expression strain by plasmid transformation. After the culture was incubated until OD reach 0.5, the culture was induced with 0.8 mM IPTG and kept for 4 h at 37° C., followed by protein extraction and purification to obtain the proteins monomer, G4P, triplex, and tetrad. The protein extraction was performed by using Capturem™ His-Tagged Purification Miniprep Kit (TAKARA).

Figure 10:
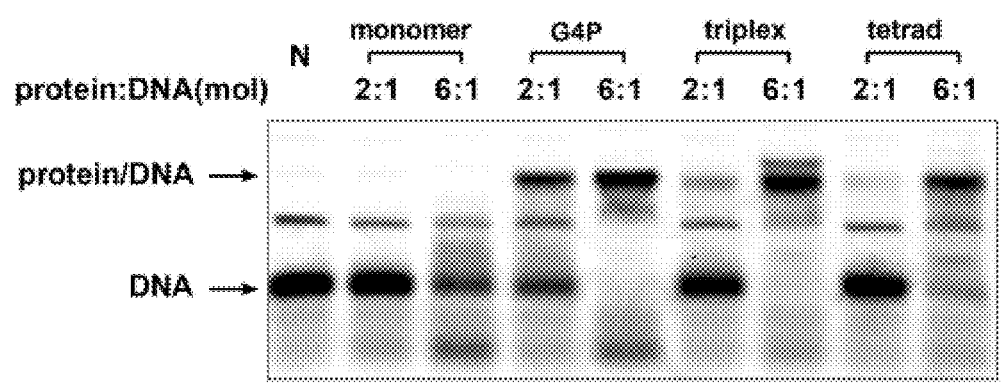
FIG. 10 shows the electrophoresis of the G4s binding to proteins monomer, G4P, triplex, and tetrad, respectively.

The obtained proteins were mixed with the DNA of G4 at a molar concentration ratio of 2:1 and 6:1, respectively, where the DNA of G4 comprises a sequence of $(GGGT)_4$ (SEQ ID NO: 74), with a concentration of 100 nM. The G4 DNAs binding to the proteins were electrophoresed in a non-denaturing polyacrylamide gel containing 75 mM KCl. FIG. 10 shows the electrophoresis of the G4s binding to proteins monomer, G4P, triplex, and tetrad, respectively. The G4 DNAs moved slower after binding to the proteins, thereby yielding a new band. The result revealed a binding ability of proteins G4P, triplex, and tetrad to G4 DNAs, among which the G4P had the highest affinity with G4s.

It will be obvious to those skilled in the art that changes and modifications may be made, and therefore, the aim in the appended claims is to cover all such changes and modifications.

What is claimed is:

1. A polypeptide probe, comprising: from two to four G4-binding domains, and one or more linkers disposed between every two G4-binding domains; each G4-binding domain comprising a specific motif comprising a sequence of amino acids PGHLKGREIGMWY (SEQ ID NO: 1).

2. The probe of claim 1, wherein each G4-binding domain comprises 23 amino acids.

3. The probe of claim 2, wherein each G4-binding domain comprises a sequence of amino acids HPGHLKGREIGMWYAKKQGQKNK (SEQ ID NO: 2).

4. The probe of claim 2, wherein the G4-binding domains are 2 in number.

5. The probe of claim 3, wherein the G4-binding domains are 2 in number.

6. The probe of claim 1, wherein the one or more linkers comprise from two to four hexapeptides each comprising a sequence of amino acids GTGSGA (SEQ ID NO: 71).

7. The probe of claim 6, wherein a number of the hexapeptides is 3.

8. The probe of claim 1, wherein the polypeptide probe further comprises a protein tag located on a C-terminal of the polypeptide probe.

9. A method for detecting G-quadruplexes (G4s) of a cell, the method comprising applying the polypeptide probe of claim 1 to a cell.

10. The method of claim 9, wherein the G4s in the cell are detected by using chromatin immunoprecipitation-next-generation sequencing (ChIP-seq).

11. The method of claim 10, wherein the cell is derived from a living human, mouse or chicken.

* * * * *